(12) United States Patent
Beira

(10) Patent No.: US 11,337,716 B2
(45) Date of Patent: *May 24, 2022

(54) SURGICAL INSTRUMENT WITH INCREASED ACTUATION FORCE

(71) Applicant: Distalmotion SA, Epalinges (CH)

(72) Inventor: Ricardo Daniel Rita Beira, Lausanne (CH)

(73) Assignee: Distalmotion SA, Epalinges (CH)

( * ) Notice: Subject to any disclaimer, the term of this patent is extended or adjusted under 35 U.S.C. 154(b) by 27 days.

This patent is subject to a terminal disclaimer.

(21) Appl. No.: 17/032,631

(22) Filed: Sep. 25, 2020

(65) Prior Publication Data

US 2021/0106348 A1    Apr. 15, 2021

Related U.S. Application Data

(63) Continuation of application No. 15/756,037, filed as application No. PCT/IB2016/001286 on Aug. 29, 2016, now Pat. No. 10,786,272.

(Continued)

(51) Int. Cl.
*A61B 17/00* (2006.01)
*A61B 17/29* (2006.01)
(Continued)

(52) U.S. Cl.
CPC .......... *A61B 17/29* (2013.01); *A61B 17/3201* (2013.01); *A61B 17/320016* (2013.01);
(Continued)

(58) Field of Classification Search
None
See application file for complete search history.

(56) References Cited

U.S. PATENT DOCUMENTS

| 2,764,301 A | 9/1956 | Goertz et al. |
| 2,771,199 A | 11/1956 | Jelatis |

(Continued)

FOREIGN PATENT DOCUMENTS

| CN | 101027010 A | 8/2007 |
| CN | 101584594 A | 11/2009 |

(Continued)

OTHER PUBLICATIONS

US 9,232,978 B2, 01/2016, Shellenberger (withdrawn)
(Continued)

*Primary Examiner* — Gary Jackson
*Assistant Examiner* — Anant A Gupta
(74) *Attorney, Agent, or Firm* — Eversheds Sutherland (US) LLP; Chistopher C. Bolten; Albert K. Heng

(57) ABSTRACT

A surgical instrument with improved end-effector gripping force. The instrument comprises a shaft, which may be inserted into a body of a patient. The articulated end-effector is mounted on the distal extremity of the instrument shaft and comprises a plurality of links interconnected by a plurality of joints, whose movements are remotely actuated by the surgeon's hands. This remote actuation is accomplished through mechanical transmission, mainly along flexible elements, which are able to deliver motion from a set of actuation elements, placed at a proximal extremity of the shaft, to the instrument's articulated end-effector. The articulated end-effector further comprises one or more cam-and-follower mechanisms that are able to amplify the force transmitted by the flexible elements so that the actuation force at the instrument jaws is maximized and the tension on the transmission elements minimized, thus increasing the fatigue resistance and life of the instrument.

18 Claims, 23 Drawing Sheets

Related U.S. Application Data

(60) Provisional application No. 62/211,019, filed on Aug. 25, 2015.

(51) Int. Cl.
*A61B 34/00* (2016.01)
*A61B 17/32* (2006.01)
*A61B 17/3201* (2006.01)
*A61B 17/34* (2006.01)
*A61B 34/30* (2016.01)

(52) U.S. Cl.
CPC .......... *A61B 17/3478* (2013.01); *A61B 34/71* (2016.02); *A61B 2017/00314* (2013.01); *A61B 2017/00323* (2013.01); *A61B 2017/00367* (2013.01); *A61B 2017/2913* (2013.01); *A61B 2017/2918* (2013.01); *A61B 2017/2919* (2013.01); *A61B 2017/2933* (2013.01); *A61B 2017/2934* (2013.01); *A61B 2017/2937* (2013.01); *A61B 2034/305* (2016.02)

(56) References Cited

U.S. PATENT DOCUMENTS

| | | |
|---|---|---|
| 2,774,488 A | 12/1956 | Goertz et al. |
| 2,846,084 A | 8/1958 | Goertz et al. |
| 3,065,863 A | 11/1962 | Saunders, Jr. et al. |
| 3,095,096 A | 6/1963 | Chesley |
| 3,212,651 A | 10/1965 | Specht et al. |
| 3,261,480 A | 7/1966 | Haaker et al. |
| 3,297,172 A | 1/1967 | Haaker et al. |
| 3,391,801 A | 7/1968 | Haaker |
| 3,425,569 A | 2/1969 | Haaker et al. |
| 4,221,516 A | 9/1980 | Haaker et al. |
| 4,756,655 A | 7/1988 | Jameson |
| 5,147,357 A | 9/1992 | Rose et al. |
| 5,176,352 A | 1/1993 | Braun |
| 5,207,114 A | 5/1993 | Salisbury, Jr. et al. |
| 5,209,747 A | 5/1993 | Knoepfler |
| 5,304,203 A | 4/1994 | El-Mallawany et al. |
| 5,308,358 A | 5/1994 | Bond et al. |
| 5,330,502 A | 7/1994 | Hassler et al. |
| 5,368,606 A | 11/1994 | Marlow et al. |
| 5,383,888 A | 1/1995 | Zvenyatsky et al. |
| 5,484,435 A | 1/1996 | Fleenor et al. |
| 5,599,151 A | 2/1997 | Daum et al. |
| 5,603,723 A | 2/1997 | Aranyi et al. |
| 5,631,973 A | 5/1997 | Green |
| 5,649,955 A * | 7/1997 | Hashimoto ............ A61B 17/29 600/562 |
| 5,649,956 A | 7/1997 | Jensen et al. |
| 5,710,870 A | 1/1998 | Ohm et al. |
| 5,716,352 A | 2/1998 | Viola et al. |
| 5,735,874 A | 4/1998 | Measamer et al. |
| 5,779,727 A | 7/1998 | Orejola |
| 5,784,542 A | 7/1998 | Ohm et al. |
| 5,792,045 A | 8/1998 | Adair |
| 5,797,900 A | 8/1998 | Madhani et al. |
| 5,810,716 A | 9/1998 | Mukherjee et al. |
| 5,810,805 A | 9/1998 | Sutcu et al. |
| 5,828,813 A | 10/1998 | Ohm |
| 5,908,436 A | 6/1999 | Cuschieri et al. |
| 5,931,832 A | 8/1999 | Jensen |
| 5,951,587 A | 9/1999 | Qureshi et al. |
| 5,976,122 A | 11/1999 | Madhani et al. |
| 6,026,701 A | 2/2000 | Reboulet |
| 6,063,095 A | 5/2000 | Wang et al. |
| 6,132,368 A | 10/2000 | Cooper |
| 6,197,017 B1 | 3/2001 | Brock et al. |
| 6,206,903 B1 | 3/2001 | Ramans |
| 6,233,504 B1 | 5/2001 | Das et al. |
| 6,281,651 B1 | 8/2001 | Haanpaa et al. |
| 6,312,435 B1 | 11/2001 | Wallace et al. |
| 6,331,181 B1 | 12/2001 | Tierney et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,371,952 B1 | 4/2002 | Madhani et al. |
| 6,394,998 B1 | 5/2002 | Wallace et al. |
| 6,435,794 B1 | 8/2002 | Springer |
| 6,436,107 B1 | 8/2002 | Wang et al. |
| 6,459,926 B1 | 10/2002 | Nowlin et al. |
| 6,491,701 B2 | 12/2002 | Tierney et al. |
| 6,554,844 B2 | 4/2003 | Lee et al. |
| 6,587,750 B2 | 7/2003 | Gerbi et al. |
| 6,594,552 B1 | 7/2003 | Nowlin et al. |
| 6,671,581 B2 | 12/2003 | Niemeyer et al. |
| 6,699,177 B1 | 3/2004 | Wang et al. |
| 6,786,896 B1 | 9/2004 | Madhani et al. |
| 6,788,999 B2 | 9/2004 | Green |
| 6,799,065 B1 | 9/2004 | Niemeyer |
| 6,840,938 B1 | 1/2005 | Morley et al. |
| 6,850,817 B1 | 2/2005 | Green |
| 6,852,107 B2 | 2/2005 | Wang et al. |
| 6,879,880 B2 | 4/2005 | Nowlin et al. |
| 6,902,560 B1 | 6/2005 | Morley et al. |
| 6,913,613 B2 | 7/2005 | Schwarz et al. |
| 6,951,535 B2 | 10/2005 | Ghodoussi et al. |
| 6,991,627 B2 | 1/2006 | Madhani et al. |
| 6,994,708 B2 | 2/2006 | Manzo |
| 7,025,064 B2 | 4/2006 | Wang et al. |
| 7,048,745 B2 | 5/2006 | Tierney et al. |
| 7,083,571 B2 | 8/2006 | Wang et al. |
| 7,090,637 B2 | 8/2006 | Danitz et al. |
| 7,101,363 B2 | 9/2006 | Nishizawa et al. |
| 7,204,836 B2 | 4/2007 | Wagner et al. |
| 7,232,440 B2 | 6/2007 | Dumbauld et al. |
| 7,241,289 B2 | 7/2007 | Braun |
| 7,306,597 B2 | 12/2007 | Manzo |
| 7,316,681 B2 | 1/2008 | Madhani et al. |
| 7,338,513 B2 | 3/2008 | Lee et al. |
| 7,364,582 B2 | 4/2008 | Lee |
| 7,373,219 B2 | 5/2008 | Nowlin et al. |
| 7,398,707 B2 | 7/2008 | Morley et al. |
| 7,481,824 B2 | 1/2009 | Boudreaux et al. |
| 7,549,998 B2 | 6/2009 | Braun |
| 7,594,912 B2 | 9/2009 | Cooper et al. |
| 7,608,039 B1 | 10/2009 | Todd |
| 7,615,002 B2 | 11/2009 | Rothweiler et al. |
| 7,615,067 B2 | 11/2009 | Lee et al. |
| 7,674,255 B2 | 3/2010 | Braun |
| 7,699,855 B2 | 4/2010 | Anderson et al. |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,890,211 B2 | 2/2011 | Green |
| 7,914,521 B2 | 3/2011 | Wang et al. |
| 7,976,458 B2 | 7/2011 | Stefanchik et al. |
| 8,048,084 B2 | 11/2011 | Schneid |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,423,186 B2 | 4/2013 | Itkowitz et al. |

(56) References Cited

U.S. PATENT DOCUMENTS

| | | |
|---|---|---|
| 8,433,389 B2 | 4/2013 | Geiger et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balan et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,860 B2 * | 8/2015 | Viola .................. A61B 17/04 |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,795,282 B2 | 10/2017 | Sholev et al. |
| 9,795,454 B2 | 10/2017 | Seeber et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 10,357,320 B2 | 7/2019 | Beira |
| 10,363,055 B2 | 7/2019 | Beira et al. |
| 10,413,374 B2 | 9/2019 | Chassot et al. |
| 10,510,447 B2 | 12/2019 | Beira et al. |
| 10,548,680 B2 | 2/2020 | Beira |
| 10,568,709 B2 | 2/2020 | Beira |
| 10,646,294 B2 | 5/2020 | Beira |
| 10,786,272 B2 * | 9/2020 | Beira .................. A61B 17/3478 |
| 10,864,049 B2 | 12/2020 | Beira |
| 10,864,052 B2 | 12/2020 | Beira |
| 11,039,820 B2 | 6/2021 | Beira |
| 11,058,503 B2 | 7/2021 | Chassot et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll et al. |
| 2003/0013949 A1 | 1/2003 | Moll et al. |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1 | 7/2008 | Brock et al. |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2009/0326552 A1 | 12/2009 | Diolaiti |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |

(56) References Cited

U.S. PATENT DOCUMENTS

| | | |
|---|---|---|
| 2010/0225209 A1 | 9/2010 | Goldberg et al. |
| 2010/0234857 A1 | 9/2010 | Itkowitz et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304070 A1* | 11/2013 | Nelson ............... A61B 17/1659 606/85 |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0277203 A1* | 9/2014 | Atoulikian ......... A61B 17/7091 606/86 A |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Mar |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0302876 A1 | 10/2016 | Teichtmann |
| 2016/0303743 A1* | 10/2016 | Rockrohr ............. B25J 15/0226 |
| 2016/0346053 A1 | 12/2016 | Beira |
| 2016/0374766 A1 | 12/2016 | Schuh |
| 2017/0020615 A1 | 1/2017 | Koenig et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0242991 A1 | 8/2018 | Beira |
| 2018/0353251 A1 | 12/2018 | Cuthbertson et al. |
| 2018/0353252 A1 | 12/2018 | Chassot et al. |
| 2018/0360548 A1 | 12/2018 | Marshall et al. |
| 2019/0133698 A1 | 5/2019 | Beira et al. |
| 2019/0239968 A1 | 8/2019 | Beira |
| 2019/0328473 A1 | 10/2019 | Chassot et al. |
| 2020/0105412 A1 | 4/2020 | Beira |

FOREIGN PATENT DOCUMENTS

| | | |
|---|---|---|
| CN | 101637402 A | 2/2010 |
| CN | 101732093 A | 6/2010 |
| CN | 103717355 A | 4/2014 |
| DE | 4303311 A1 | 8/1994 |
| DE | 19652792 C2 | 5/1999 |
| DE | 10314827 B3 | 4/2004 |
| DE | 10314828 B3 | 7/2004 |
| DE | 102012222755 A1 | 6/2014 |
| DE | 102014205036 A1 | 9/2015 |
| DE | 102014205159 A1 | 9/2015 |
| EP | 0595291 A1 | 5/1994 |
| EP | 0621009 A1 | 10/1994 |
| EP | 0677275 A2 | 10/1995 |
| EP | 0776739 A2 | 6/1997 |
| EP | 1254642 A1 | 11/2002 |
| EP | 1279371 B1 | 12/2004 |
| EP | 1886630 A2 | 2/2008 |
| EP | 1889579 A2 | 2/2008 |
| EP | 1889583 A1 | 2/2008 |
| EP | 2058090 A2 | 5/2009 |
| EP | 1977677 B1 | 8/2009 |
| EP | 2095778 A1 | 9/2009 |
| EP | 1889583 B1 | 4/2011 |
| EP | 2377477 B1 | 5/2012 |
| EP | 2473119 A2 | 7/2012 |
| EP | 2305144 B1 | 10/2012 |
| EP | 2044893 B1 | 7/2013 |
| EP | 2653110 A1 | 10/2013 |
| EP | 2679192 A2 | 1/2014 |
| EP | 2736680 A2 | 6/2014 |
| EP | 2777561 A1 | 9/2014 |

(56) References Cited

FOREIGN PATENT DOCUMENTS

| | | |
|---|---|---|
| EP | 2783643 A1 | 10/2014 |
| EP | 2837340 A1 | 2/2015 |
| EP | 2837354 A1 | 2/2015 |
| EP | 2554131 B1 | 8/2015 |
| EP | 2777561 B1 | 10/2015 |
| EP | 2979657 A1 | 2/2016 |
| EP | 2837340 B1 | 10/2016 |
| EP | 2783643 B1 | 1/2019 |
| GB | 834244 A | 5/1960 |
| GB | 969899 A | 9/1964 |
| JP | 2004041580 A | 2/2004 |
| JP | 2007290096 A | 11/2007 |
| JP | 2008104620 A | 5/2008 |
| JP | 2009018027 A | 1/2009 |
| KR | 20110032444 A | 3/2011 |
| KR | 20130031403 A | 3/2013 |
| SU | 722754 A1 | 3/1980 |
| WO | WO-8200611 A1 | 3/1982 |
| WO | WO-9743942 A1 | 11/1997 |
| WO | WO-9825666 A1 | 6/1998 |
| WO | WO-03067341 A2 | 8/2003 |
| WO | WO-03086219 A2 | 10/2003 |
| WO | WO-2004052171 A2 | 6/2004 |
| WO | WO-2005009482 A2 | 2/2005 |
| WO | WO-2005046500 A1 | 5/2005 |
| WO | WO-2006086663 A2 | 8/2006 |
| WO | WO-2007133065 A1 | 11/2007 |
| WO | WO-2008130235 A2 | 10/2008 |
| WO | WO-2009091497 A2 | 7/2009 |
| WO | WO-2009095893 A2 | 8/2009 |
| WO | WO-2009145572 A2 | 12/2009 |
| WO | WO-2009157719 A2 | 12/2009 |
| WO | WO-2010019001 A2 | 2/2010 |
| WO | WO-2010030114 A2 | 3/2010 |
| WO | WO-2010050771 A2 | 5/2010 |
| WO | WO-2010083480 A2 | 7/2010 |
| WO | WO-2010096580 A1 | 8/2010 |
| WO | WO-2010130817 A1 | 11/2010 |
| WO | WO-2011025818 A1 | 3/2011 |
| WO | WO-2011027183 A2 | 3/2011 |
| WO | WO-2011123669 A1 | 10/2011 |
| WO | WO-2012020386 A1 | 2/2012 |
| WO | WO-2012049623 A1 | 4/2012 |
| WO | WO-2013007784 A1 | 1/2013 |
| WO | WO-2013014621 A2 | 1/2013 |
| WO | WO-2014012780 A1 | 1/2014 |
| WO | WO-2014018447 A1 | 1/2014 |
| WO | WO-2014067804 A1 | 5/2014 |
| WO | WO-2014094716 A1 | 6/2014 |
| WO | WO-2014094717 A1 | 6/2014 |
| WO | WO-2014094718 A1 | 6/2014 |
| WO | WO-2014094719 A1 | 6/2014 |
| WO | WO-2014139023 A1 | 9/2014 |
| WO | WO-2014145148 A2 | 9/2014 |
| WO | WO-2014156221 A1 | 10/2014 |
| WO | WO-2014201010 A1 | 12/2014 |
| WO | WO-2014201538 A1 | 12/2014 |
| WO | WO-2015081946 A1 | 6/2015 |
| WO | WO-2015081947 A1 | 6/2015 |
| WO | WO-2015088647 A1 | 6/2015 |
| WO | WO-2015088655 A1 | 6/2015 |
| WO | WO-2015111475 A1 | 7/2015 |
| WO | WO-2015113933 A1 | 8/2015 |
| WO | WO-2015129383 A1 | 9/2015 |
| WO | WO-2015139674 A1 | 9/2015 |
| WO | WO-2015175200 A1 | 11/2015 |
| WO | WO-2016030767 A1 | 3/2016 |
| WO | WO-2016083189 A1 | 6/2016 |
| WO | WO-2016097861 A1 | 6/2016 |
| WO | WO-2016097864 A2 | 6/2016 |
| WO | WO-2016097868 A1 | 6/2016 |
| WO | WO-2016097871 A1 | 6/2016 |
| WO | WO-2016097873 A2 | 6/2016 |
| WO | WO-2016154173 A1 | 9/2016 |
| WO | WO-2016162751 A1 | 10/2016 |
| WO | WO-2016162752 A1 | 10/2016 |
| WO | WO-2016183054 A1 | 11/2016 |
| WO | WO-2016189284 A1 | 12/2016 |
| WO | WO-2016209891 A1 | 12/2016 |
| WO | WO-2017015599 A1 | 1/2017 |
| WO | WO-2017037532 A1 | 3/2017 |
| WO | WO-2017064301 A1 | 4/2017 |
| WO | WO-2017064303 A1 | 4/2017 |
| WO | WO-2017064305 A1 | 4/2017 |
| WO | WO-2017064306 A1 | 4/2017 |
| WO | WO-2017134077 A1 | 8/2017 |
| WO | WO-2017220978 A1 | 12/2017 |
| WO | WO-2018142112 A1 | 8/2018 |
| WO | WO-2018162921 A1 | 9/2018 |
| WO | WO-2019099346 A2 | 5/2019 |
| WO | WO-2020131304 A1 | 6/2020 |
| WO | WO-2020263870 A1 | 12/2020 |

OTHER PUBLICATIONS

U.S. Appl. No. 13/878,924 / U.S. Pat. No. 10,092,359, filed May 17, 2013 / Oct. 9, 2018.
U.S. Appl. No. 14/233,184 / U.S. Pat. No. 9,696,700, filed Jan. 16, 2014 / Jul. 4, 2017.
U.S. Appl. No. 15/116,509 / U.S. Pat. No. 10,265,129, filed Aug. 3, 2016 / Apr. 23, 2019.
U.S. Appl. No. 15/506,659 / U.S. Pat. No. 10,357,320, filed Feb. 24, 2017 / Jul. 23, 2019.
U.S. Appl. No. 15/536,539 / U.S. Pat. No. 10,864,049, filed Jun. 15, 2017 / Dec. 15, 2020.
U.S. Appl. No. 15/536,562 / U.S. Pat. No. 10,864,052, filed Jun. 15, 2017 / Dec. 15, 2020.
U.S. Appl. No. 15/536,568 / U.S. Pat. No. 10,548,680, filed Jun. 15, 2017 / Feb. 4, 2020.
U.S. Appl. No. 15/536,573, filed Jun. 15, 2017.
U.S. Appl. No. 15/536,576 / U.S. Pat. No. 10,646,294, filed Jun. 15, 2017 / May 12, 2020.
U.S. Appl. No. 15/564,193 / U.S. Pat. No. 10,568,709, filed Oct. 3, 2017 / Feb. 25, 2020.
U.S. Appl. No. 15/564,194 / U.S. Pat. No. 10,363,055, filed Oct. 3, 2017 / Jul. 30, 2019.
U.S. Appl. No. 15/633,611 / U.S. Pat. No. 10,325,072, filed Jun. 26, 2017 / Jun. 18, 2019.
U.S. Appl. No. 15/756,037 / U.S. Pat. No. 10,786,272, filed Feb. 27, 2018 / Sep. 29, 2020.
U.S. Appl. No. 15/976,812, filed May 10, 2018.
U.S. Appl. No. 16/153,695, filed Oct. 5, 2018.
U.S. Appl. No. 16/269,383 / U.S. Pat. No. 10,413,374, filed Feb. 6, 2019 / Sep. 17, 2019.
U.S. Appl. No. 16/389,854, filed Apr. 19, 2019.
U.S. Appl. No. 16/442,435 / U.S. Pat. No. 10,510,447, filed Jun. 14, 2019 / Dec. 17, 2019.
U.S. Appl. No. 16/505,585, filed Jul. 8, 2019.
U.S. Appl. No. 16/701,063, filed Dec. 2, 2019.
U.S. Appl. No. 16/870,870, filed May 8, 2020.
Abbott, et al., Design of an Endoluminal Notes Robotic System, IEEE/RSJ International Conference on Intelligent Robots and Systems, 2007, San Diego, CA (pp. 410-416).
Aesculap Surgical Technologies, Aesculap.RTM. Caiman.RTM., Advanced Bipolar Seal and Cut Technology Brochure, 6 pages (retrieved Aug. 31, 2015).
Arata, et al., Development of a dexterous minimally-invasive surgical system with augmented force feedback capability, IEEE/RSJ International Conference on Intelligent Robots and Systems, 2005 (pp. 3207-3212).
Cavusigky, et al., Laparoscopic Telesurgical Workstation, IEEE Transactions on Robotics and Automation, (15)4:728-739 (1999).
Charles, et al., Dexterity-enhanced Telerobotic Microsurgery, 8th International Conference Advanced Robotics, pp. 5-10 (1997).
Dachs, et al., Novel Surgical Robot Design: Minimizing the Operating Envelope With in the Sterile Field, 28th International Conference, IEEE Engineering in Medicine Biology Society, 2006, New York (pp. 1505-1508).

(56) References Cited

OTHER PUBLICATIONS

Dario, et al., "Novel Mechatronic Tool for Computer-Assisted Arthroscopy," IEEE Transactions on Information Technology in Biomedicine, 4(1):15-29 (Mar. 2000).
Extended European Search Report dated Mar. 18, 2020 in EP Patent Appl. Serial No. 19213231.4 (1031).
Focacci, et al., Lightweight Hand-held Robot for Laparoscopic Surgery, IEEE International Conference on Robotics & Automation, Rome, Italy, pp. 599-604 (2007).
Guthart, et al., The Intuitive.TM. Telesurgery System: Overview and Application, IEEE International Conference on Robotics & Automation, San Francisco, CA, 2000 (pp. 618-621).
Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).
Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).
International Search Report & Written Opinion dated Feb. 2, 2017 in Int'l PCT Patent Appl. Serial No. PCT/IB2016/001286 (1310).
International Search Report & Written Opinion dated Jan. 18, 2013 in Int'l PCT Patent Appl Serial No. PCT/IB2012/053786 (0310).
International Search Report & Written Opinion dated Jul. 10, 2018 in Int'l PCT Patent Appl. Serial No. PCT/IB2018/053272 (1410).
International Search Report & Written Opinion dated Jun. 10, 2016 in Int'l PCT Patent Appl Serial No. PCT/IB2015/002533 (0810).
International Search Report & Written Opinion dated Jun. 13, 2016 in Int'l PCT Patent Appl Serial No. PCT/IB2015/002493 (0710).
International Search Report & Written Opinion dated Mar. 30, 2015 in Int'l PCT Patent Appl Serial No. PCT/EP2015/051473 (0410).
International Search Report & Written Opinion dated May 23, 2016 in Int'l PCT Patent Appl Serial No. PCT/IB2015/002524 (0610).
International Search Report & Written Opinion dated May 24, 2016 in Int'l PCT Patent Appl Serial No. PCT/IB2015/002487 (0910).
International Search Report & Written Opinion dated Sep. 2, 2016 in Int'l PCT Patent Appl Serial No. PCT/IB2016/000543 (1110).
International Search Report & Written Opinion dated Feb. 17, 2016 in Int'l PCT Patent Appl. Serial No. PCT/IB2015/002095 (0510).
International Search Report & Written Opinion dated Mar. 23, 2012 in Int'l PCT Patent Appl. Serial No. PCT/IB2011/054476 (0210).
International Search Report & Written Opinion dated Jul. 7, 2020 in Int'l. PCT Patent Appl. Serial No. PCTIB2020050039 (1610).
International Search Report & Written Opinion dated Jul. 23, 2019 in Int'l PCT Patent Appl. No. PCT/IB2019/050961 (1510).
International Search Report & Written Opinion dated Aug. 25, 2016 in Int'l PCT Patent Appl. Serial No. PCT/IB2016/000542 (1210).
Ishii, et al., Development of a New Bending Mechanism and Its Application to Robotic Forceps Manipulator, IEEE International Conference on Robotics & Automation, Rome, Italy, 2007 (pp. 238-243).
International Search Report & Written Opinion dated Apr. 26, 2016 in Int'l PCT Patent Appl. Serial No. PCT/IB2015/002512 (1010).
Kobayashi, et al., Small Occupancy Robotic Mechanisms for Endoscopic Surgery, International Conference on Medical Image Computing and Computer assisted Interventions, 2002, (pp. 75-82).

Lang, et al., Intra-operative robotics: NeuroArm., Acta Neurochir Suppl, 109:231 -236 (2011).
Mayer, et al., The Endo[PA]R System for Minimally Invasive Robotic Surgery, IEEE/RSJ International Conference on Intelligent Robots and Systems, Sendai, Japan, 2004 (pp. 3637-3642).
Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).
Mitsuishi, et al., Master-Slave Robotic Platform and its Feasibility Study for Micro-Neurosurgery, Int. J. Med. Robot., 9(2):180-9 (2013).
Morita, et al., Microsurgical Robotic System for the Deep Surgical Field: development of a Prototype and Feasibility Studies in Animal and Cadaveric Models, J. Neurosurg., 103(2):320-7 (2005).
Nakamura, et al., Multi-DOF Forceps Manipulator System for Laparoscopic Surgery-Mechanism miniaturized & Evaluation of New Interface, 4th International Conference on Medical Image Computing and Computer assisted Interventions (MICCAI2001), 2001 (pp. 606-613).
Peirs, et al., "Design of an Advanced Tool Guiding System for Robotic Surgery," IEEE International Conference on Robotics & Automation, Taipei, Taiwan, 2003, (pp. 2651-2656).
Salle, et al., Optimal Design of High Dexterity Modular MIS Instrument for Coronary Artery Bypass Grafting, IEEE International Conference on Robotics & Automation, New Orleans, LA, 2004, (pp. 1276-1281).
Seibold, et al., Prototype of Instrument for Minimally Invasive Surgery with 6-Axis Force Sensing Capability, IEEE International Conference on Robotics & Automation, Barcelona, Spain, 2005, (pp. 496-501).
Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).
Stryker.RTM., Endoscopy, Take a Look Around, Ideal Eyes.TM. FFD122 HD, Articulating Laparoscope Brochure, 2 pages (2009).
Swiss Search Report dated Jun. 4, 2012 in Swiss Patent Application No. CH 00702/12.
Tavakoli, et al., Force Reflective Master-Slave System for Minimally Invasive Surgery, IEEE/RSJ International Conference on Intelligent Robots and Systems, Las Vegas, NV, 2003, (pp. 3077-3082).
Taylor, et al., Steady-Hand Robotic System for Microsurgical Augmentation, The International Journal of Robotics Research, 18(12):1201-1210 (1999).
www.cttc.co/technologies/maestro-non-robotic-dexterous-laproscopic-instrum- ent-writs-providing-seven-degrees, Maestro: Non-Robotic Dexterous Laproscopic Instrument With a Wrist Providing Seven Degrees of Freedom, accessed Nov. 12, 2015, 4 pages.
Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).
Zeus., Robotic Surgical System, available at http://allaboutroboticsurgery.com/zeusrobot.html.

\* cited by examiner

SURGICAL INSTRUMENT WITH INCREASED ACTUATION FORCE

CROSS-REFERENCE TO RELATED APPLICATIONS

This application is a continuation of U.S. patent application Ser. No. 15/756,037, filed Feb. 27, 2018, now U.S. Pat. No. 10,786,272, which is a national phase of International PCT Patent Application Serial No. PCT/IB2016/001286, filed Aug. 29, 2016, which claims priority to U.S. Provisional Patent Application Ser. No. 62/211,019, filed Aug. 28, 2015, the entire contents of each of which are incorporated herein by reference.

FIELD OF THE INVENTION

The present invention relates to the field of remotely actuated mechanical systems, more particularly to endoscopic or minimally invasive mechanisms, and most particularly to remotely actuated minimally invasive surgical instruments. More specifically, this invention relates to minimally invasive articulated surgical instruments such as graspers, needle holders, and scissors, wherein the orientation of end-effectors in relation to the instrument shaft is able to be controlled. Most specifically, the invention relates to mechanisms wherein the actuation and orientation of the instrument's distal end-effector is remotely performed, from the proximal to the distal extremity of the instrument shaft, by mechanical transmission elements.

BACKGROUND OF THE INVENTION

Open surgery is still the standard technique for most surgical procedures. It has been used by the medical communication for several decades and consists of performing surgical tasks by making a relatively long incision in the abdomen or other body cavity or area, through which traditional surgical tools are inserted. However, due to the long incision, this approach is extremely invasive for the patient, resulting in substantial blood loss during the surgery and long and painful recovery periods in an in-patient setting.

In order to provide an alternative to the invasiveness of open surgery, laparoscopy, a minimally invasive technique, was developed. Instead of a single long incision, one or more smaller incisions are made in the patient through which long and thing surgical instruments and endoscopic cameras are made in the patient through which long and thin surgical instruments and endoscopic cameras are inserted. Because of the low degree of invasiveness, laparoscopic techniques reduce blood loss and pain while also shortening hospital stays. When performed by experienced surgeons, these techniques can attain clinical outcomes similar to open surgery. However, despite the above-mentioned advantages, laparoscopy requires advanced surgical skills to manipulate the rigid and long instrumentation through small incisions in the patient. As such, adoption rates for minimally invasive techniques in complex procedures are lower than would be desirable.

Traditionally, laparoscopic instruments, such as graspers, dissectors, scissors and other tools, have been mounted on straight shafts. These shafts are inserted through small incisions into the patient's body and, because of that, their range of motion inside the body is reduced. The entry incision acts as a point of rotation, decreasing the freedom for positioning, actuating, articulating and orientating the instruments inside the patient. Also, the use of straight-shafted instruments prevents bending or articulation inside the surgical space. Therefore, due to the challenges facing traditional minimally invasive instrumentation, laparoscopic procedures are mainly limited to use in simple surgeries, while only a small minority of surgeons is able to use them in complex procedures.

Accordingly, there is a clear need for providing distal articulations to effector elements of laparoscopic instruments, allowing the distal end-effector elements to be articulated with respect to the longitudinal axis of the instrument shaft. This enables the surgeon to reach the tissue of interest at a full range of angles, including oblique angles, with respect to the longitudinal axis of the shaft. In addition, the instrument should be able to fully operate its effector elements at such angulations.

Although several articulated "wristed" instruments have been proposed using rigid mechanical transmission (U.S. Pat. Nos. 5,330,502, 7,819,894, 7,674,255), flexible mechanical transmission is considered by many to exhibit better performance characteristics in terms of weight, friction and other attributes (WO9743942, U.S. Pat. Nos. 6,394, 998, 6,554,844).

When metallic ropes are used with a suitable strand construction, flexible mechanical transmission can provide a fairly good axial stiffness with an acceptable radial (bending) flexibility. However, the life of the metallic ropes used in instruments employing flexible mechanical transmission is strongly affected by the value of the maximum tension to which they are exposed during their normal use. When metallic ropes are passed around pulleys, their constituent strands are forced to rub against each other, increasing the friction on the overall system, thus impacting mechanical transmission and causing the ropes to wear during several cycles of utilization. Therefore, the higher the tension on the ropes, the higher the friction on the system and the shorter the life of the instrument. Metallic ropes in pulley-driven systems can also be subject to stretching over time, thus resulting in a progressive reduction in actuation force at the end-effector over time. These considerations relating to friction, cable wear and cable stretching must be acknowledged in view of the mechanical constraints of cable-driven mechanical systems with pulleys, in which the force applied to system cables is not necessarily reflected at the end effector, typically being reduced as a function of the number of pulleys and links in the system. This phenomenon is described in greater detail in the following paragraphs with reference to a prior disclosure by the present applicants.

In the present applicants' previous disclosure, a cable-driven surgical instrument 120, has a main shaft 121 that allows the passage of flexible elements 124, 125, 126 that are able to transmit motion to three different end-effector links 127, 128, 129, from the proximal hub 123 at the articulated end-effector 122 of the instrument 120 (FIGS. 23 and 24 hereto).

As can be seen in FIGS. 25 and 26 hereto, the distal end-effector members 128, 129 are operatively connected to flexible members 125 and 126 so that they can be independently rotated in both directions along the distal axis 130. Contact between the flexible elements and the distal end-effector elements is made by way of the end effector pulleys 128a, 129a (FIG. 27 hereto), which are part of (or rigidly attached to) the end-effector links 128, 129. Then, by the combination of rotations of the two distal end-effector links 128, 129, it is possible to actuate the surgical instrument 120 in order to accomplish its function (FIG. 28 hereto).

An issue with the aforementioned system is related to the fact that the actuation forces applied at the tip of the instrument jaws are only a fraction of the forces to which the cables are exposed. This phenomenon is explained in FIG. 29 hereto, comprising a free body diagram of one of the distal end-effector members 129, applying a force F, measured at a point two thirds of the way to the distal end of its blade length, on a body 131. By considering the equilibrium of torques at the axis of rotation 130 and, for instance, a ratio of L/R=3 (wherein L is the distance from the axis of rotation 130 to the point of measurement of the applied force F and R is the radius of the effector pulley 129a), the tension T in the cable will be three times higher than the force F at the tip. This limitation can be problematic when high gripping forces are required at the distal end-effector tip of the instrument jaws 128, 129 (for instance, in needle holders). In cases such as these where high gripping forces are required, it is possible that enough force simply cannot be applied to the cables to achieve the necessary gripping force or, in the alternative, sufficient force can be applied but the resulting strain on the cables is too high, resulting in unacceptable wear or stretching as discussed above. Using the example of a needle holder, the forces applied at the proximal end of the instrument (provided by the hand of the user of by an actuator) have to be extremely high in order to avoid undesired movements of the needle (if sufficient force can be applied to avoid undesired movements), which can negatively impact the life of the instrument.

Accordingly, an aim of the present invention is to overcome the aforementioned drawbacks of known devices in certain articulated instrument applications by providing a new articulated end-effector mechanism, preferably to be used in a cable-driven surgical instrument. The new articulated end-effector mechanism should be capable of providing enough force to the instrument's distal jaws, especially when high actuation forces at the distal extremity of the instrument jaws are required and the usable life of the instrument has to be maximized. In addition, another aim of the present invention is to reduce the input forces required to actuate the instrument, resulting in more comfort to the user (if the instrument is fully mechanical) or less power required from the actuators (if the instrument if robotic).

SUMMARY OF THE INVENTION

Theses aims and other advantages are achieved by a new articulated end-effector mechanism, designed to be used at the distal extremity of a surgical instrument shaft, in the form of, for example, a needle holder, scissor or grasper. The shaft defines the longitudinal axis of the instrument and is able to move according to the mobility constraints imposed by a body incision, which include a rotational movement about its own axis. This rotation also causes the rotation of the end-effector, mounted on the distal extremity of the shaft. Thus, the instrument shaft has the combined function of positioning the end-effector within the interior of the patient's body and allowing the passage of the different mechanical elements that are able to actuate the different distal end-effector articulations, by transmitting motion from the proximal extremity of the instrument shaft, to the distal end-effector articulations. These distal articulations of the end-effector are able to (1) actuate the surgical instrument in order to accomplish its function (for example, grasping or cutting) and (2) provide orientation motions between the end effector and the instrument shaft.

The actuation movement of each distal jaw of the end-effector is originated by an input movement on the proximal extremity of the instrument shaft, which is connected to a cam-and-follower mechanism, placed on the instrument's end-effector, by flexible transmission elements passing through the instrument shaft. This cam-and-follower mechanism is then able to transmit, and amplify, the force to a distal end-effector link (or jaw) by direct contact.

This mechanism is intended to be used primarily in surgical procedures, where the instruments with articulated end-effectors are passing through incisions into a patient's body. It is also adapted for any suitable remote actuated application requiring a dexterous manipulation with high stiffness and precision such as, but in no way limited to, assembly manipulation, manipulation in narrow places, manipulation in dangerous or difficult environments, and manipulation in contaminated or sterile environments.

BRIEF DESCRIPTION OF FIGURES

The invention will be better understood according to the following detailed description of several embodiments with reference to the attached drawings, in which.

DETAILED DESCRIPTION OF THE INVENTION

Figure 1:
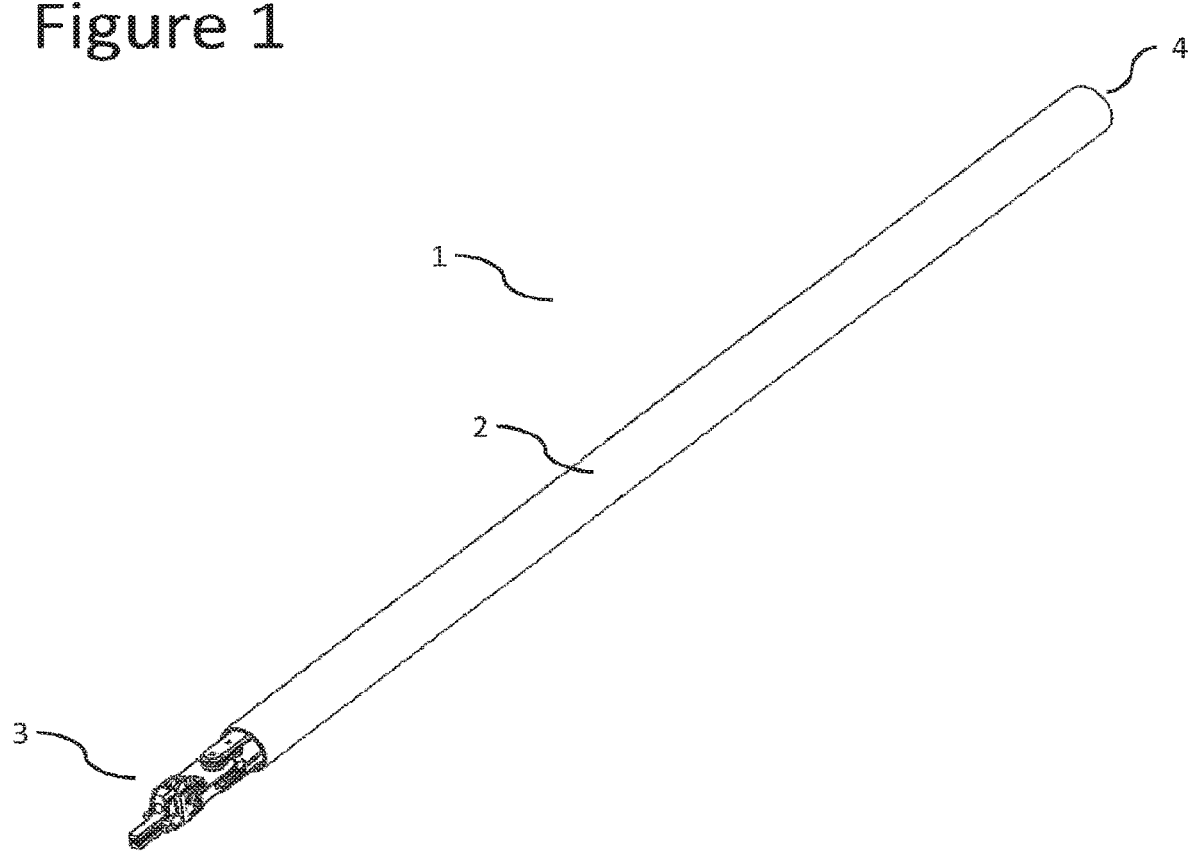
FIG. 1 shows a perspective view of a surgical instrument including an articulated end-effector according to an embodiment of the invention.
Figure 2:
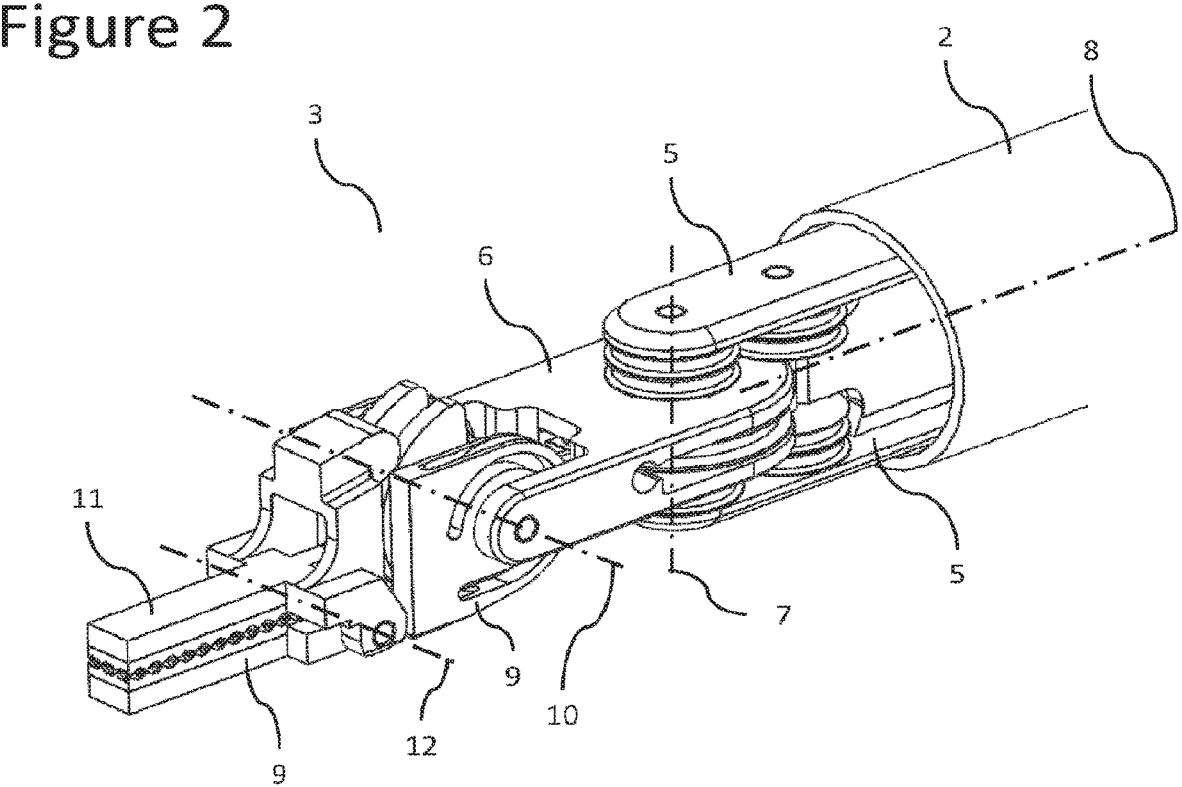
FIG. 2 shows a perspective view of an articulated end-effector of a surgical instrument according to an embodiment of the invention.

With general reference to FIG. 1, a surgical instrument 1 for minimally invasive surgical procedures, with an articulated end-effector constructed in accordance with an embodiment of the present invention, is described herein. This instrument 1 includes a main shaft 2 with a distal end-effector 3 and a proximal extremity 4 or head. Referring to FIG. 2, the end-effector 3 is connected to the distal extremity 20 of the main shaft 2 by a proximal joint, which allows the rotation of a proximal end-effector link 6 around a proximal axis 7 in such a manner that the orientation of the proximal end-effector link 6 with respect to the main shaft axis 8 can be changed.

Referring to FIG. 2, a second end-effector link 9 is rotatably connected to the proximal end-effector link 6 by a second end-effector joint, which is represented by the second end-effector axis 10. This second end-effector axis 10 is substantially perpendicular and non-intersecting with the proximal axis 7 and substantially intersects the main shaft axis 8.

Referring to FIG. 2, the distal end-effector link 11 is rotatably connected to the second end-effector link 9 by a distal end-effector joint, which is represented by the distal end-effector axis 12. This distal end-effector axis 12 is substantially parallel to the second end-effector axis 10 and perpendicular and non-intersecting with the proximal end-effector axis 7.

Figure 3:
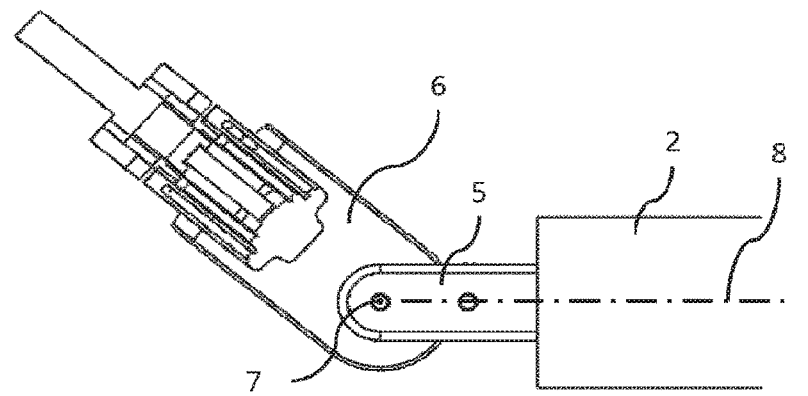
FIG. 3 shows the articulated end-effector of FIG. 2 in a first active position.
Figure 4:
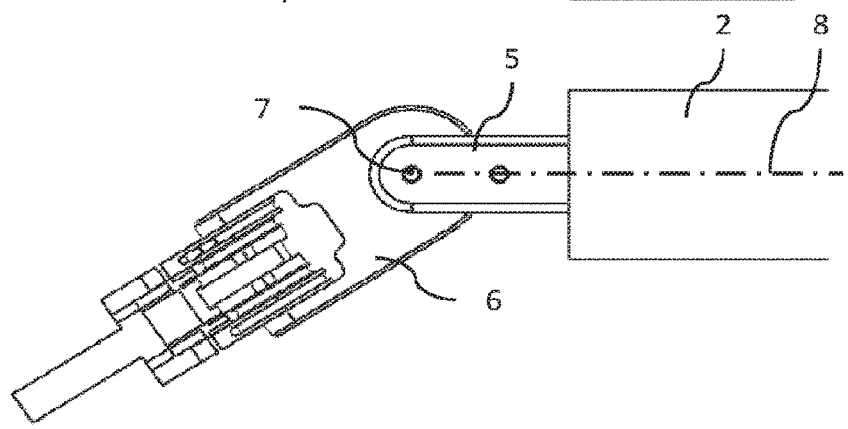
FIG. 4 shows the articulated end-effector of FIG. 2 in a second active position.

By actuating the proximal joint, the proximal end-effector link 6 can be angulated over the proximal axis 7, in the range of up to ±90°, with respect to the plane containing the main shaft axis 8 and the proximal axis 7, thus providing a first orientational degree of freedom for the end effector 3. FIGS. 3 and 4 show a surgical instrument 1 according to an embodiment of the present invention with different angular displacements at the proximal joint.

Figure 5:
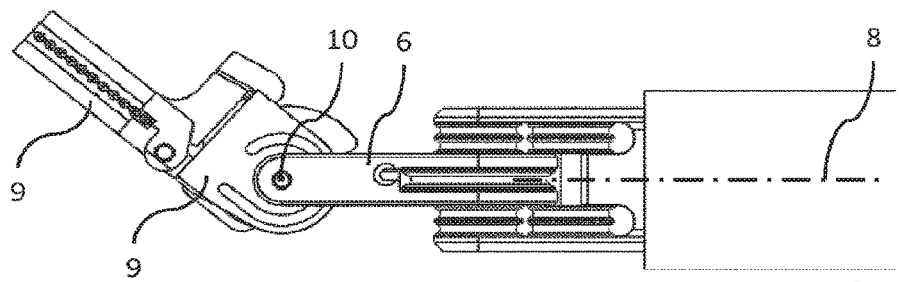
FIG. 5 shows the articulated end-effector of FIG. 2 in a third active position.
Figure 6:
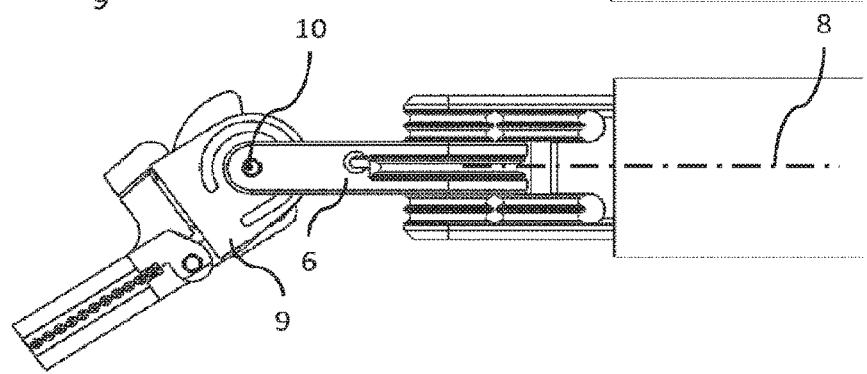
FIG. 6 shows the articulated end-effector of FIG. 2 in a fourth active position.

By actuating the second end-effector joint, the second end-effector link 9 can be angulated, substantially up to ±90°, over the second end-effector axis 10, with respect to the plane containing the main shaft axis 8 and the second end-effector axis 10, thus providing a second orientational degree of freedom for the end effector 3 that is perpendicular to the aforementioned first orientational degree of freedom. FIGS. 5 and 6 show a surgical instrument 1 according to an embodiment of the present invention with different angular displacements at the second end-effector joint.

Figure 7:
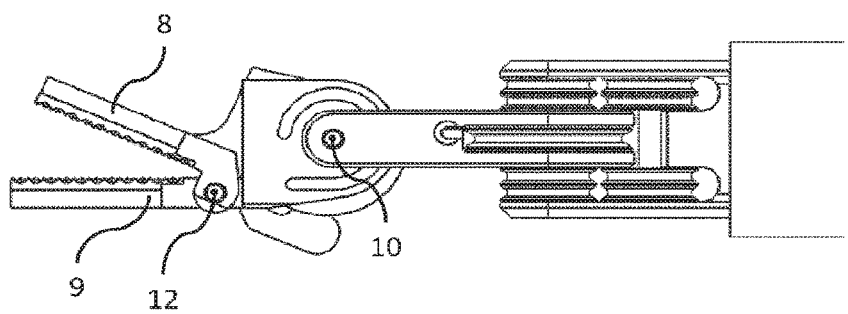
FIG. 7 shows the articulated end-effector of FIG. 2 in a sixth active position.
Figure 8:
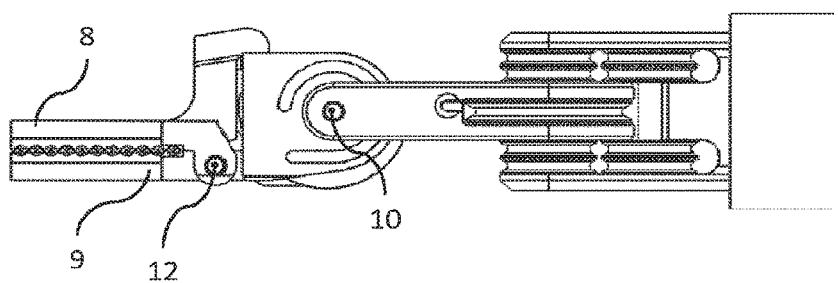
FIG. 8 shows the articulated end-effector of FIG. 2 in a seventh active position.

By actuating the distal end-effector joint, the distal end-effector link 11 can be angulated, over the distal end-effector axis 12, so that the surgical instrument is actuated in order to accomplish its function (for instance as a needle holder, scissors or forceps), thus providing an actuation degree of freedom at the end effector 3. FIGS. 7 and 8 show the surgical instrument 1 with different angular displacements at the distal end-effector joint.

Figure 9:
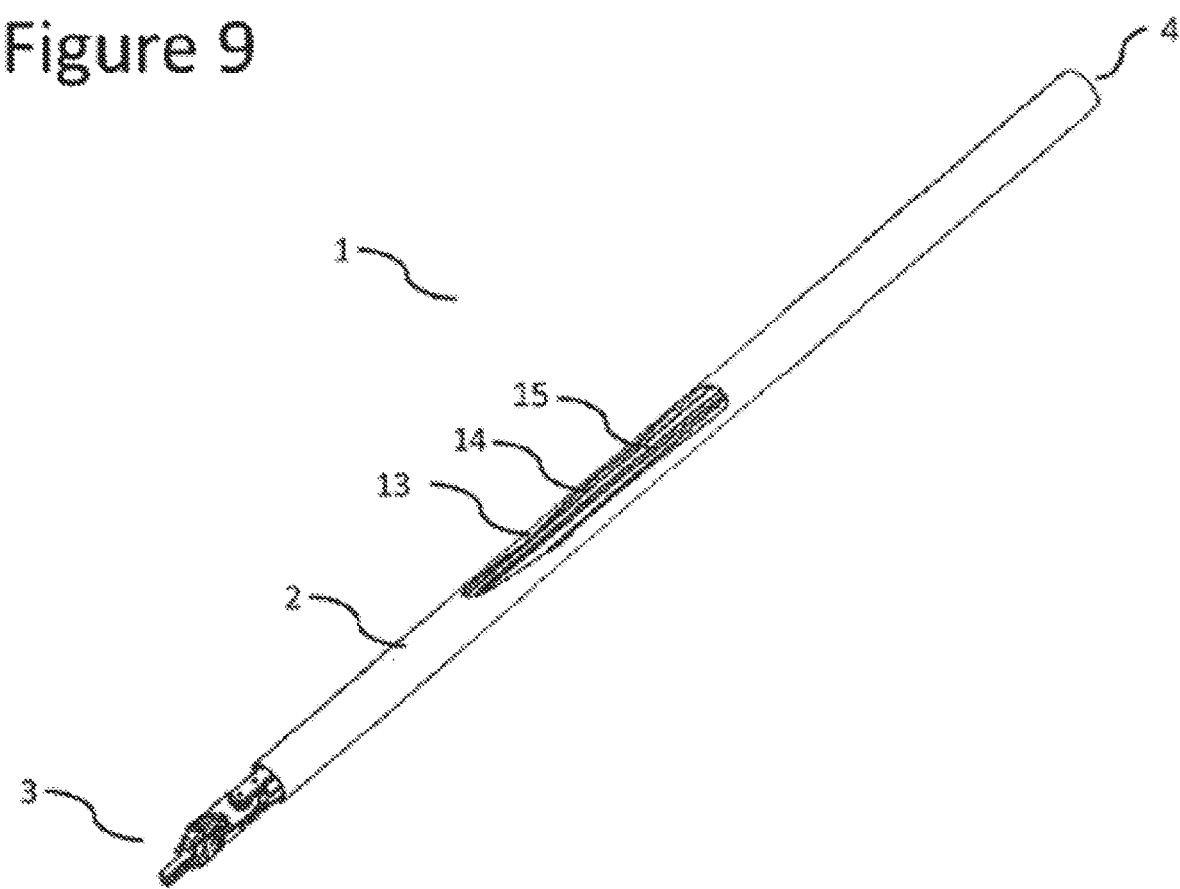
FIG. 9 shows a perspective view of the surgical instrument of FIG. 1 with a schematic cutout of an outer tube of the longitudinal shaft of the surgical instrument, through which is it possible to see the different flexible mechanical transmission elements.

With reference to FIG. 9, the main shaft 2 allows the passage of flexible elements 13, 14, 15 that are able to deliver motion to the different end-effector links 6, 9, 11, from the proximal extremity 4 or head of the instrument shaft 2. The flexible elements 13, 14, 15, may optionally take the form of metal ropes or cables which may be constructed of tungsten, steel or any other metal suitable for surgical applications.

Figure 10:
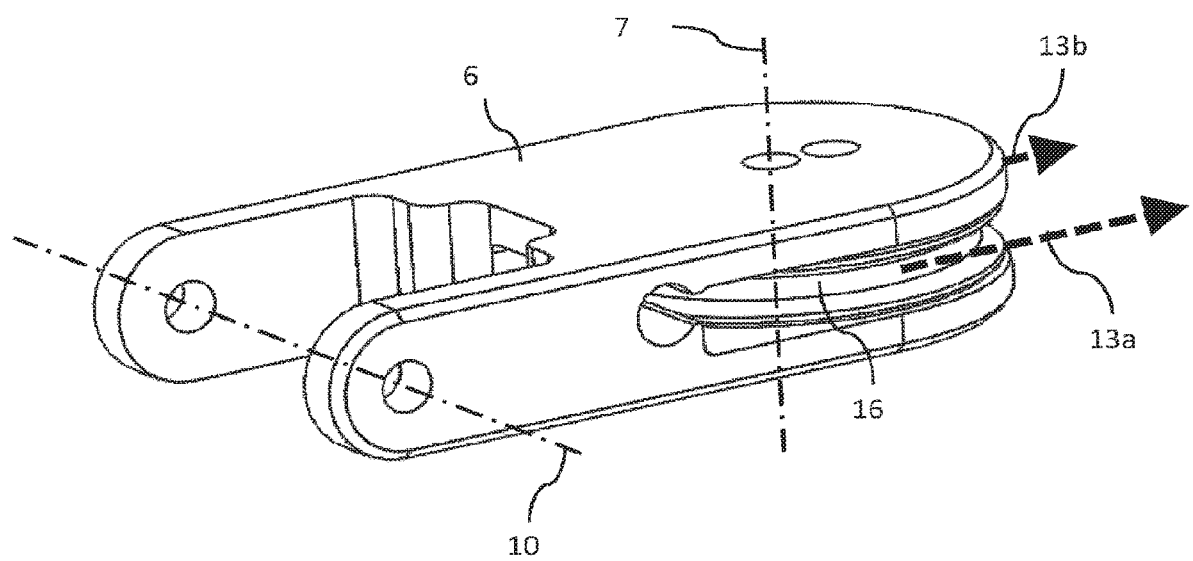
FIG. 10 shows actuation topology for a distal end-effector link according to an embodiment of the invention.

As can be seen in FIG. 10, the flexible element 13 comprises two different segments, 13a, 13b, which form a closed cable loop between the proximal end-effector link 6 and an input element at the proximal extremity 4 of the instrument shaft 2. The proximal end-effector link 6 is operatively connected to the flexible members 13a and 13b so that it can be independently rotated in both directions along the proximal axis 7. The contact between the flexible elements 13a, 13b and the proximal end-effector link 6 is made in a grooved pulley 16, which is rigidly attached or operably connected to the proximal end-effector link 6.

Figure 11:
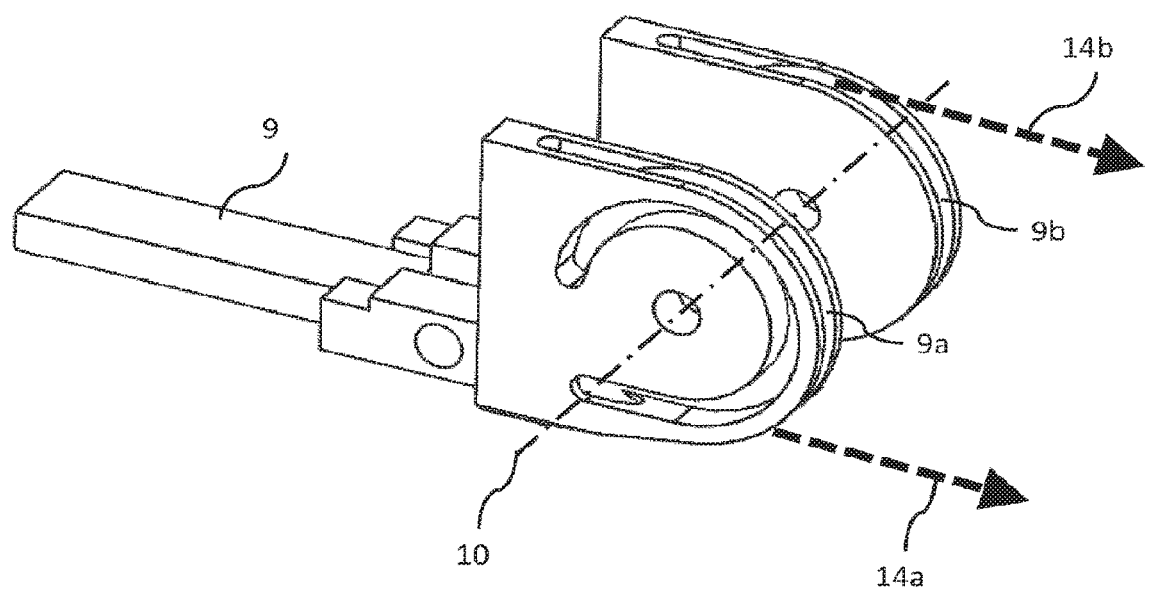
FIG. 11 shows actuation topology for a second end-effector link according to an embodiment of the invention.

As can be seen in FIG. 11, the flexible element 14 comprises two different segments, 14a, 14b, which form a closed cable loop between the proximal end-effector link 6 and an input element at the proximal extremity 4 of the instrument shaft 2. The second end-effector link 9 is operatively connected to the flexible members 14a and 14b so that it can be independently rotated in both directions along the second end-effector axis 10. The contact between the flexible elements 14a, 14b and the second end-effector link 9 is made in the grooved surfaces 9a, 9b, which have a pulley-like geometry and are part of the second end-effector link 9.

Figure 12:
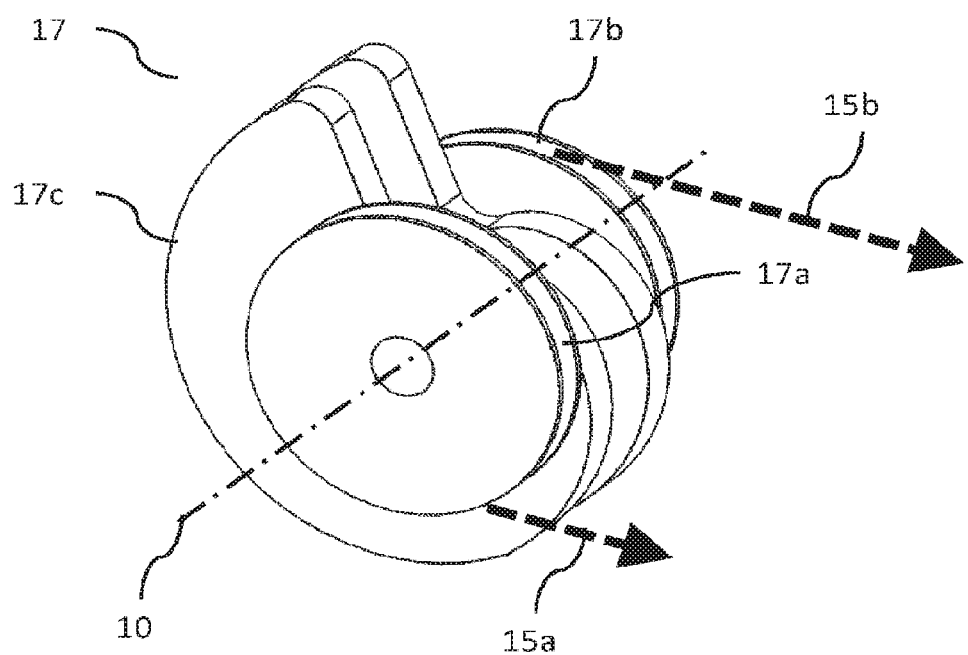
FIG. 12 shows actuation topology for a cam element of a cam-and-follower mechanism according to an embodiment of the invention.
Figure 13:
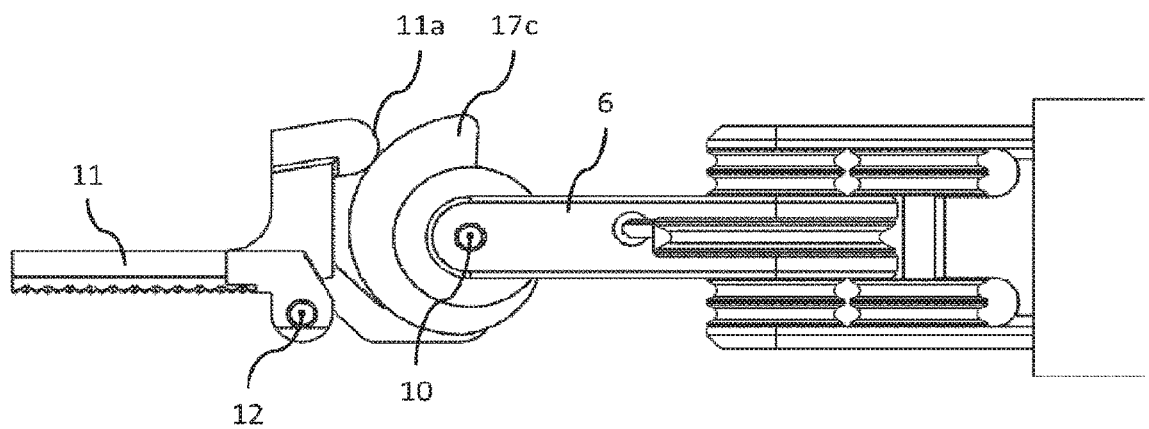
FIG. 13 shows a side view of a cam-and-follower mechanism actuating a distal articulation of an instrument's end-effector according to an embodiment of the invention.
Figure 14:
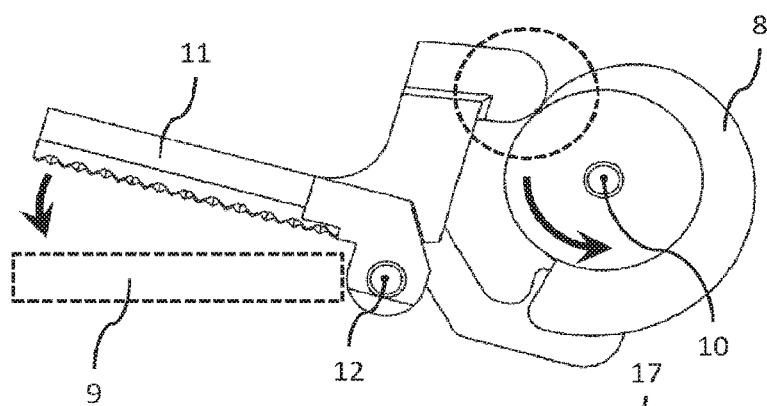
FIG. 14 shows the cam-and-follower mechanism of FIG. 13 in a first active position.
Figure 15:
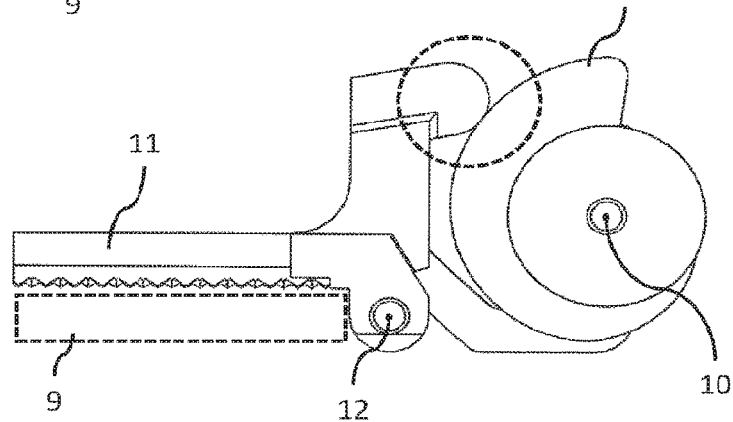
FIG. 15 shows the cam-and-follower mechanism of FIG. 13 in a second active position.

In order to increase the actuation (or gripping) force at the distal jaws 9, 11, while decreasing the tension in the flexible transmission elements, a cam-and-follower mechanism is used at the instrument's articulated end-effector 3. It comprises a cam element 17 (FIG. 12), having 2 grooved surfaces 17a, 17a, with pulley-like geometry, to which the flexible members 15a and 15b are attached, so that it can be independently rotated in both directions along the second end-effector axis 10. Rigidly attached or operably connected to these pulley-like geometries 17a, 17b (or components), a cam-profile geometry 17c (or component) is also able to rotate in both directions along the second end-effector axis 10. Another element of the cam-and-follower mechanism is the follower geometry 11a (or component), which is part of (or rigidly attached to) the distal end-effector link 11 (FIG. 13). By being in contact with the cam-profile geometry 17c of the cam element 17, the follower geometry 11a (and therefore, necessarily, the distal end-effector link 11) is driven to rotate against the second end-effector element 9 when the cam element 17 is rotating (shown in counter-clockwise rotation in FIGS. 14 and 15). This movement of the distal jaws 9, 11 moving against each other corresponds to the actuation of the surgical instrument 1, wherein the actuation force can be maximized by a careful selection of the profile of the cam element 17.

In some embodiments of the current invention, by way of example but not limitation, the cam element 17 may have a spiral profile (FIG. 16), whose rotation is able to drive the movement of the follower geometry 11a or component with a force that is much higher than the tension in the flexible element 15 that is driving the rotation. As a consequence, the instrument will be able to deliver high actuation forces at the jaws, while keeping the tension in the cables at more minimal values, which increases the fatigue performance and available usage cycles of the instrument and decreases the overall friction in the system.

Figure 16:
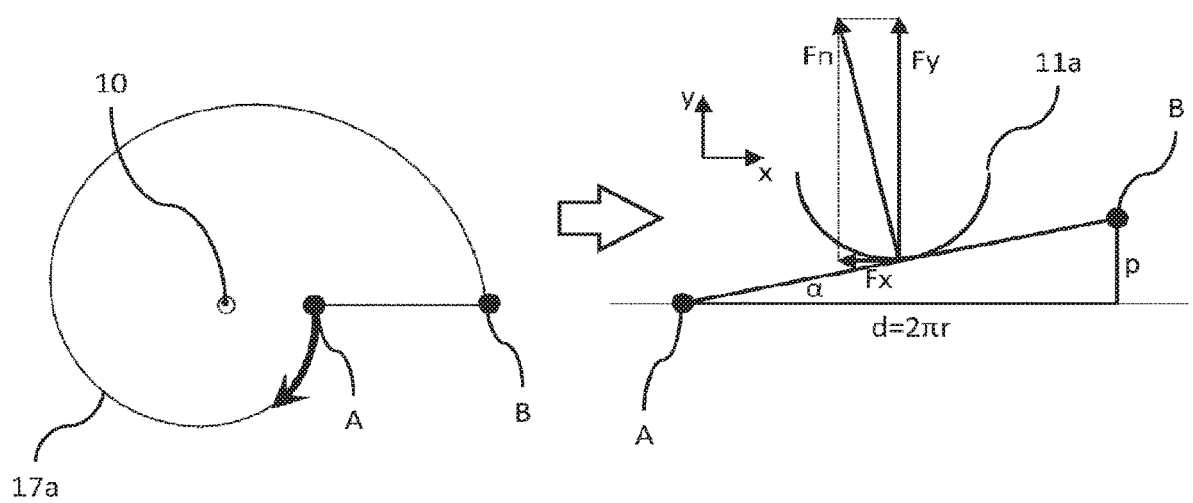
FIG. 16 illustrates the phenomenon of force amplification of a cam-and-follower mechanism with a single-pitch spiral-profile cam element according to an embodiment of the invention.

This aforementioned force multiplication phenomenon can be better understood with the example of the wedge analogy of FIG. 16. With reference to the above embodiment, the rotation of the spiral cam element 17 so that the point of contact with the follower geometry 11a or component is traveling from point A to point B, is equivalent to driving along a y vector a follower geometry 11a or component by moving a wedge along an x vector and having the point of contact travelling from point A to point B. The angle α of the wedge is optimally a function of the pitch of the spiral and its initial radius. The smaller the angle of the wedge, the higher the multiplication of forces, from cable tension to actuation force. Thus, variation of the wedge angle (by varying spiral pitch and initial spiral radius) can be used to ultimately control the degree of force multiplication and, consequently, the degree of reduction in cable tension.

Figure 17:
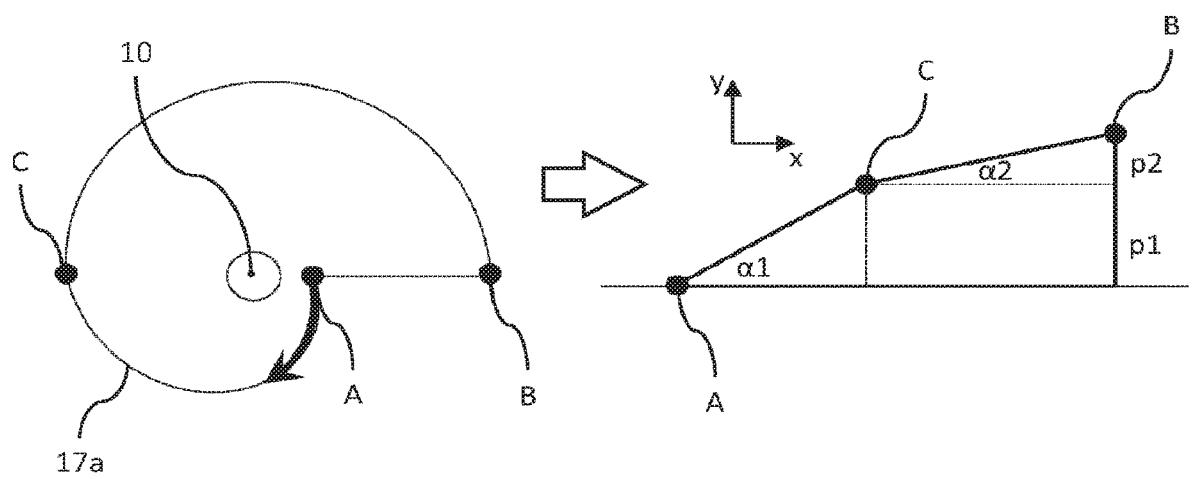
FIG. 17 illustrates the phenomenon of force amplification of a cam-and-follower mechanism with a dual-pitch spiral-profile cam element according to an embodiment of the invention.

FIG. 17 shows an alternate embodiment of the current invention, where the cam profile 17a comprises different spiral profiles (from A to C and from C to B), with different pitches p1, p2. In the same way, in other embodiments of the current invention, a wide variety of shapes and profiles can be used in the cam element 17 to drive the follower geometry 11a to move according to different movement and force patterns.

Figure 18:
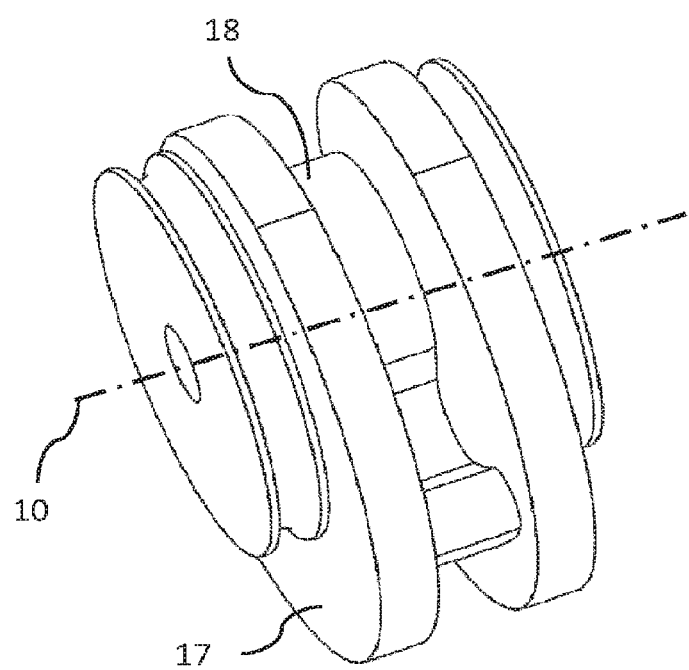
FIG. 18 shows a perspective view of two cam elements (reverse and actuation) rigidly attached, according to an embodiment of the invention.
Figure 19:
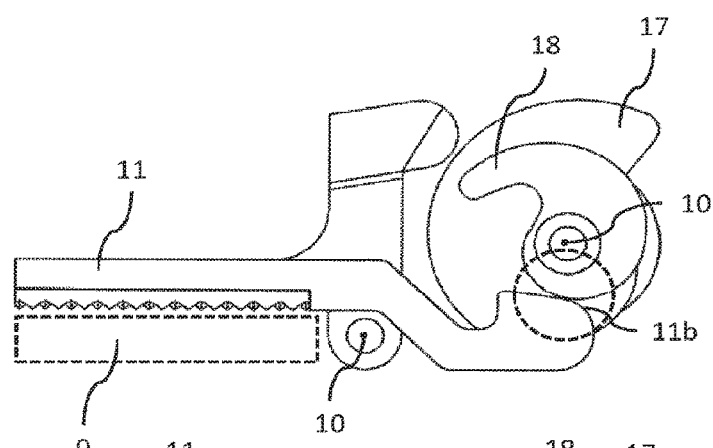
FIG. 19 shows a reverse cam-and-follower mechanism in a first active position according to the embodiment shown in FIG. 18.
Figure 20:
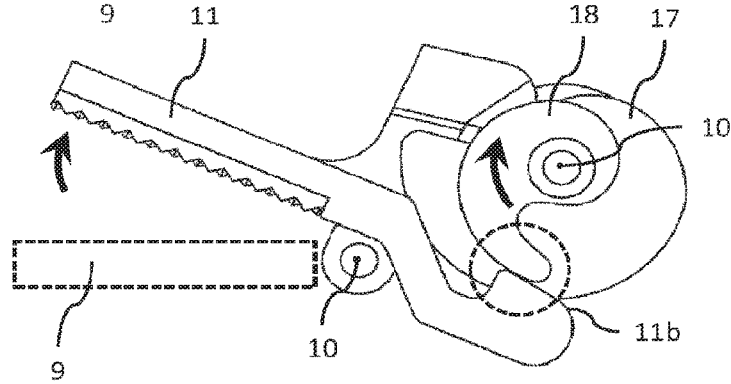
FIG. 20 shows a reverse cam-and-follower mechanism in a second active position according to the embodiment shown in FIG. 19.

In a further alternate embodiment, and in order to reverse the movement of the jaws, a second cam-and-follower mechanism can be used. FIG. 18 shows how a reverse cam element 18 can be fixed to the actuation cam element 17 so that both cam profiles are able to rotate about the same axis 10. By being in contact with the cam element 18, the follower geometry 11b (and therefore the distal end-effector link 11) is driven to rotate away from the second end-effector element 9 when the cam element is rotating (shown rotating in a clockwise direction in FIGS. 19 and 20).

Figure 21:
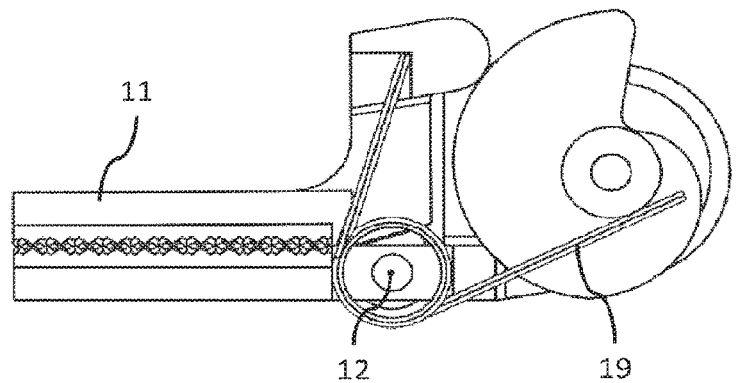
FIGS. 21 and 22 show an embodiment of the current invention with a spring element to reverse the actuation movement, in two different working positions.
Figure 22:
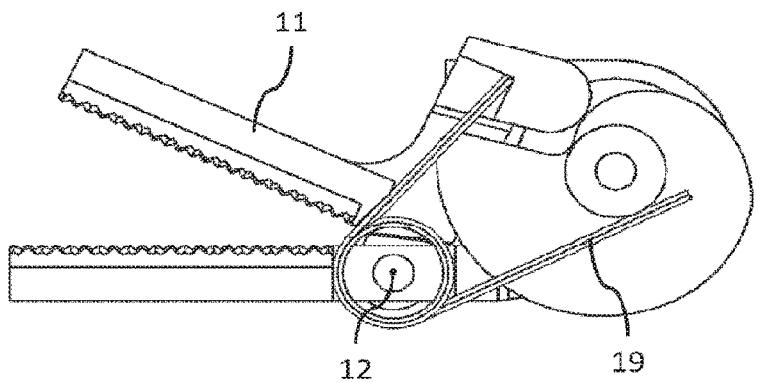
Figure 23:
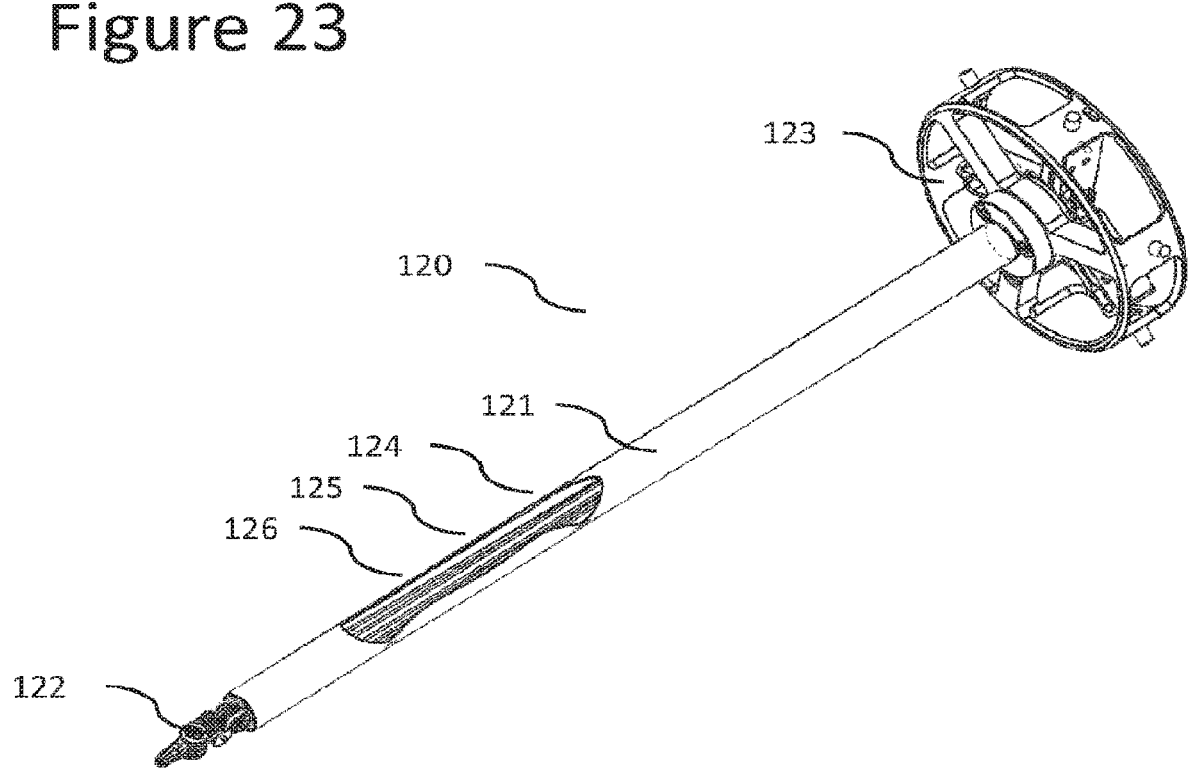
FIG. 23 shows a perspective view of a surgical instrument previously disclosed by Applicants.
Figure 24:
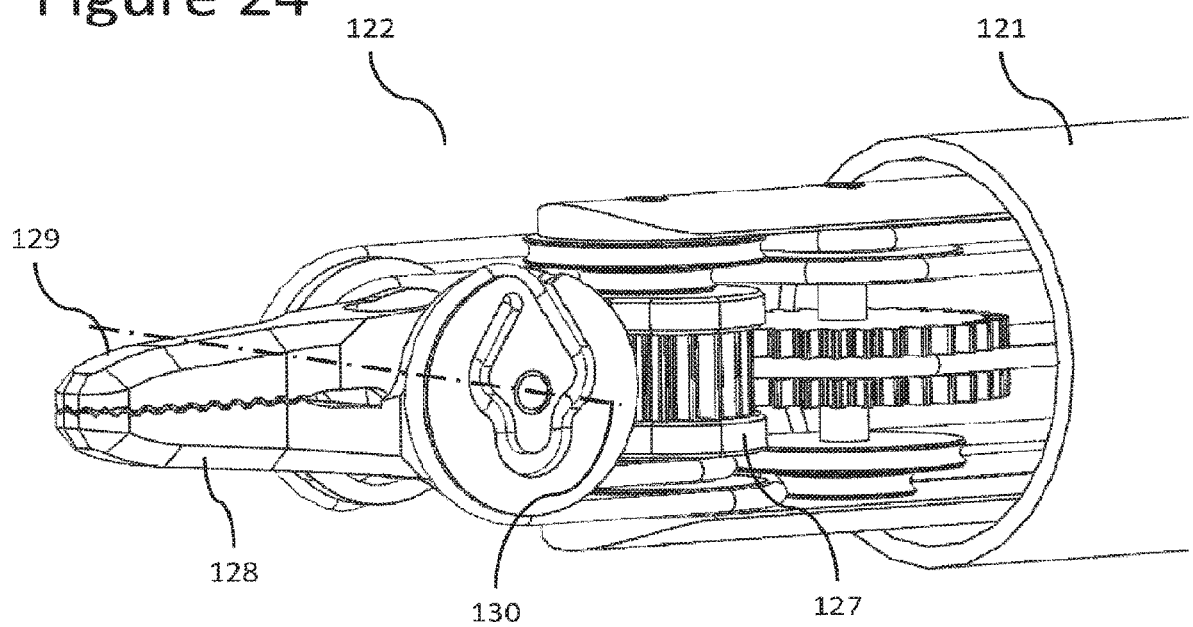
FIG. 24 shows a perspective view of an articulated end-effector of the surgical instrument shown in FIG. 23.
Figure 25:
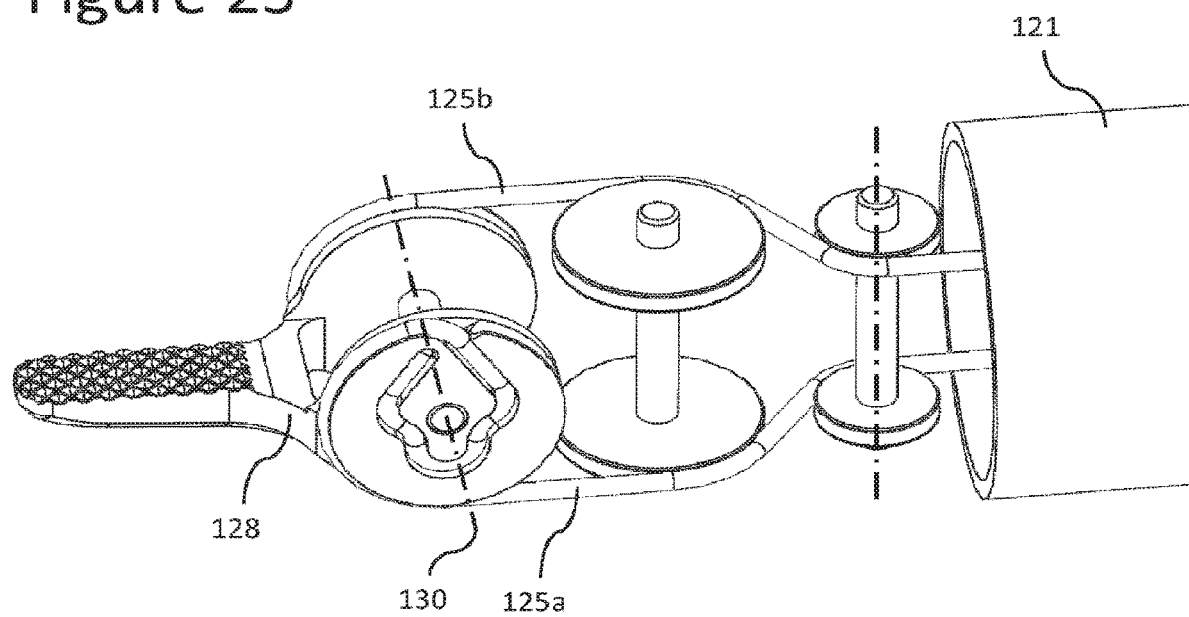
FIG. 25 shows the actuation topology for a first distal end-effector link of the surgical instrument shown in FIG. 23.
Figure 26:
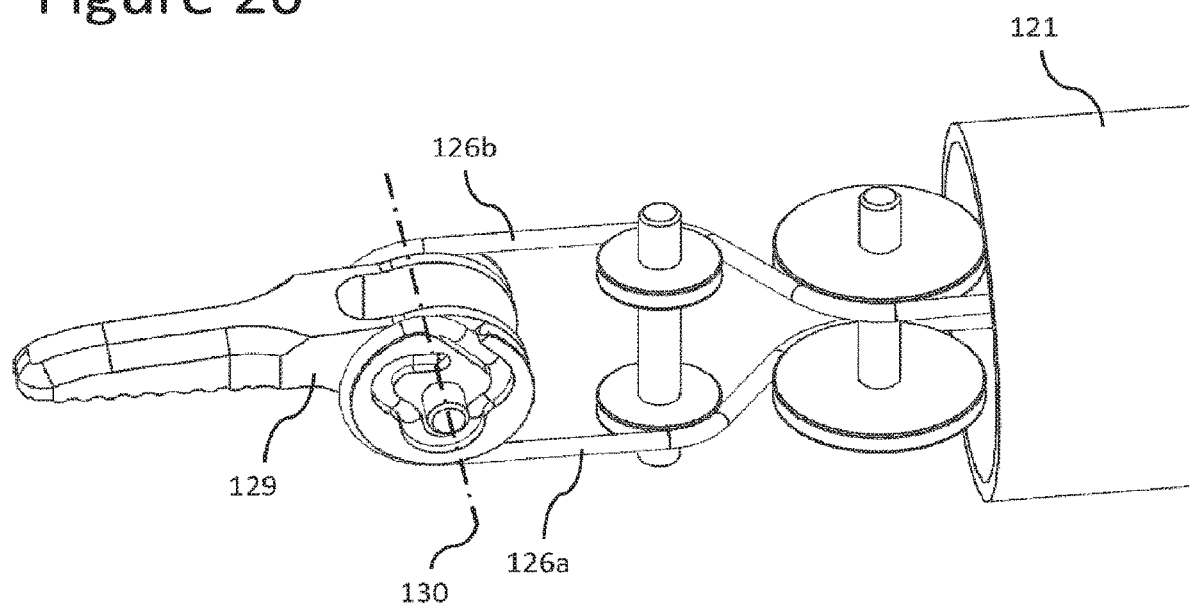
FIG. 26 shows the actuation topology for a second distal end-effector link of the surgical instrument shown in FIG. 23.
Figure 27:
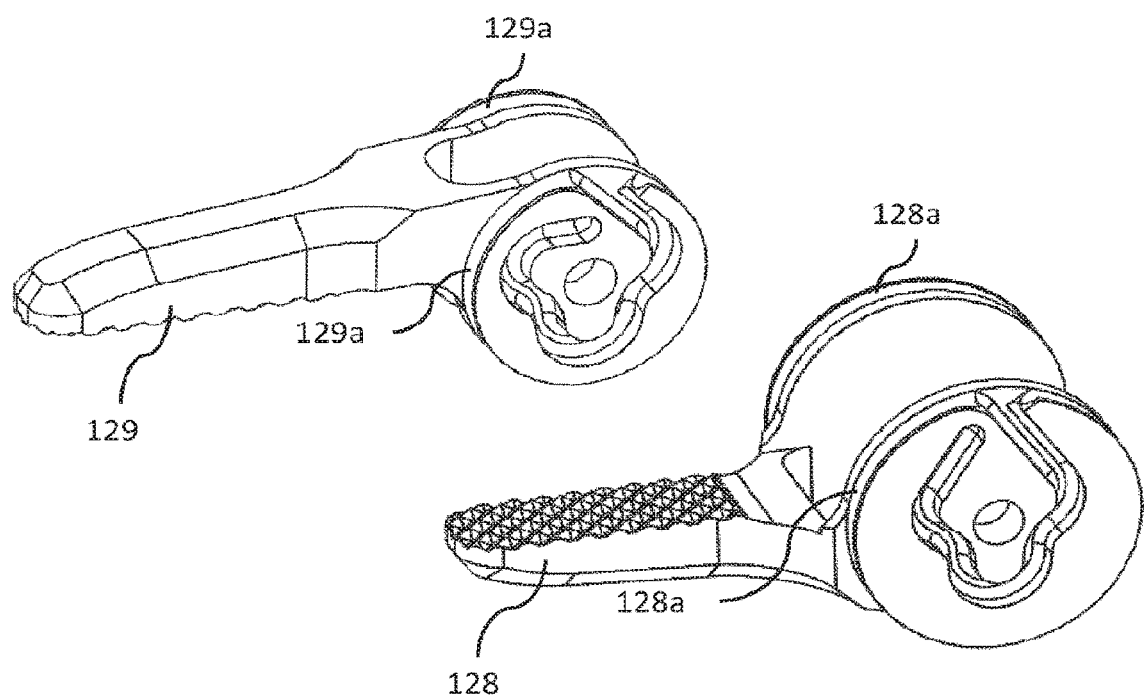
FIG. 27 shows a perspective views of the two distal end-effector links of the surgical instrument shown in FIG. 23.
Figure 28:
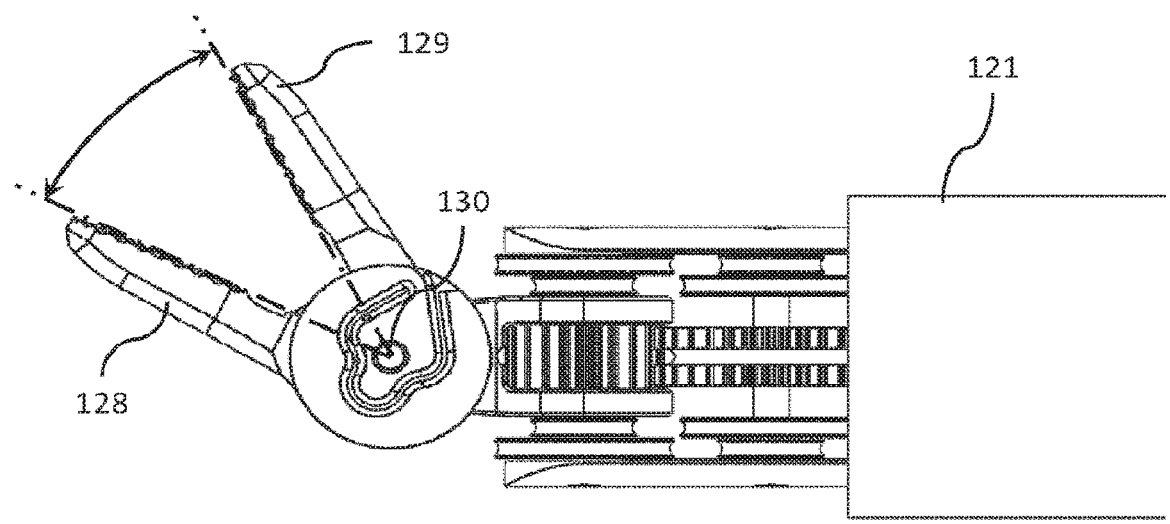
FIG. 28 shows the articulated end-effector of the surgical instrument shown m FIG. 23 achieving an actuation by the movement of the distal end-effector links.
Figure 29:
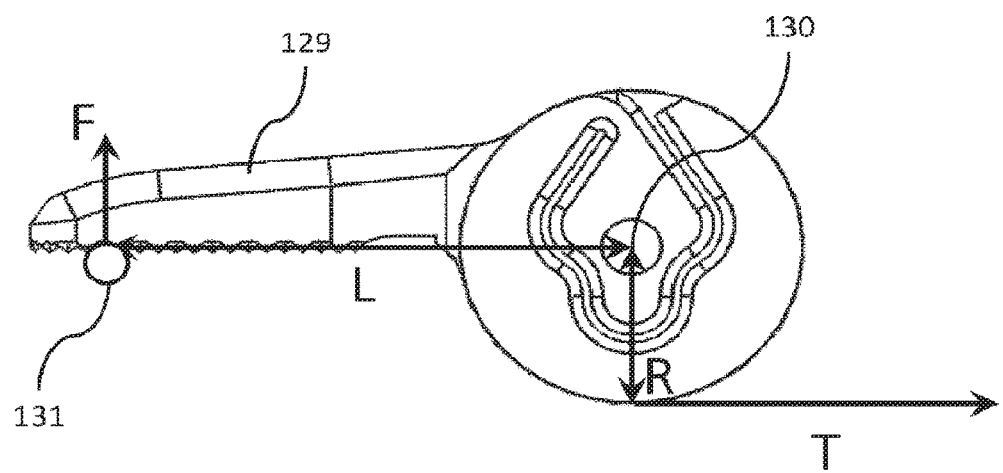
FIG. 29 shows a free body diagram of one of the distal end-effector members of the surgical instrument shown in FIG. 23.

In yet another embodiment of the current invention, the reverse movement can be achieved not by a second cam-and-follower mechanism but by a spring element 19, which is able to rotate (about the axis 12) the distal end-effector link 11 back to its open position, when the cam element 17 rotates back (shown rotating clockwise in FIGS. 21 and 22) and the follower geometry 11a loses contact with the cam-profile geometry 17c of the cam element 17.

While this invention has been shown and described with reference to particular embodiments thereof, one of skill in the art will readily realise that various changes in form and details will be possible without departing from the spirit and scope of the invention as defined by the appended claims. Solely by way of example, one of skill in the art will understand that various geometries are possible for the cam-and-follower elements and that various angles are possible for the wedge element, thus impacting the force multiplication effect of the inventive system.

What is claimed is:

1. An articulated surgical instrument comprising:
    an end-effector comprising one or more end-effector links, the one or more end-effector links comprising one or more follower geometries;
    a cam comprising one or more spiral profiles rotatably coupled to the one or more follower geometries; and
    flexible mechanical transmissions coupled to the cam, the flexible mechanical transmissions configured to rotate the cam to thereby actuate the end-effector with an increased actuation force and with a reduced tension on the flexible mechanical transmissions via the one or more follower geometries.

2. The articulated surgical instrument of claim 1, further comprising a longitudinal instrument shaft having a lumen configured to receive the flexible mechanical transmissions.

3. The articulated surgical instrument of claim 2, further comprising a proximal extremity, and wherein the flexible mechanical transmissions are configured to transmit motion from the proximal extremity to the end-effector through the lumen of the longitudinal instrument shaft.

4. The articulated surgical instrument of claim 1, wherein a first end-effector link of the one or more end-effector links is rotatably coupled to a second end-effector link of the one or more end-effector links via an end-effector joint.

5. The articulated surgical instrument of claim 4, wherein the end-effector joint is positioned distal to the one or more follower geometries and the cam.

6. The articulated surgical instrument of claim 1, wherein the increased actuation force at the end-effector is higher than the reduced tension on the flexible mechanical transmissions.

7. The articulated surgical instrument of claim 1, wherein rotation of the cam by the flexible mechanical transmissions is configured to increase fatigue performance of the articulated surgical instrument.

8. The articulated surgical instrument of claim 1, wherein rotation of the cam by the flexible mechanical transmissions is configured to increase usage cycles of the articulated surgical instrument.

9. The articulated surgical instrument of claim 1, wherein rotation of the cam by the flexible mechanical transmissions is configured to decrease overall friction of the articulated surgical instrument.

10. The articulated surgical instrument of claim 1, wherein rotation of the cam by the flexible mechanical transmissions is configured to drive movement of the one or more follower geometries along the one or more spiral profiles of the cam.

11. The articulated surgical instrument of claim 1, wherein the flexible mechanical transmissions comprise at least one of cables or metal ropes.

12. The articulated surgical instrument of claim 1, wherein variances in any of spiral pitch, initial spiral radius and spiral angle of the one or more spiral profiles influence a degree of the increased actuation force at the end-effector.

13. The articulated surgical instrument of claim 1, wherein the one or more end-effector links provide at least 2 orientational degrees of freedom and at least one actuation degree of freedom.

14. A method of actuating an end-effector of an articulated surgical instrument, the method comprising:

actuating flexible mechanical transmissions to rotate a cam comprising one or more spiral profiles rotatably coupled to one or more follower geometries of one or more end-effector links of the end-effector to thereby drive movement of the one or more follower geometries along the one or more spiral profiles of the cam and actuate the end-effector with an increased actuation force and with a reduced tension on the flexible mechanical transmissions via the one or more follower geometries.

15. The method of claim 14, wherein the increased actuation force is higher than the reduced tension on the flexible mechanical transmissions.

16. The method of claim 14, wherein actuating the flexible mechanical transmissions to rotate the cam increases fatigue performance of the articulated surgical instrument.

17. The method of claim 14, wherein actuating the flexible mechanical transmissions to rotate the cam actuates the end-effector in at least one of two or more orientational degrees of freedom or one or more actuation degrees of freedom.

18. The method of claim 14, further comprising varying any of spiral pitch, initial spiral radius and spiral angle of the one or more spiral profiles to influence a degree of increased actuation force at the end-effector.

* * * * *